(12) United States Patent
Leclerc et al.

(10) Patent No.: US 9,963,669 B2
(45) Date of Patent: May 8, 2018

(54) FACILITY FOR COUPLING A BIOREACTOR WITH A DEVICE FOR PHYSICOCHEMICALLY ANALYSING OR COLLECTING SAMPLES

(71) Applicants: Universite Technologie de Compiegne—UTC, Compiegne (FR); Centre National de la Recherche Scientifique (CNRS), Paris (FR)

(72) Inventors: Eric Leclerc, Margny les Compiegne (FR); Patrick Paullier, Thourotte (FR); Franck Merlier, Monchy Humiere (FR)

(73) Assignees: Universite Technologie De Compiegne—UTC (FR); Centre National de la Recherche Scientifique (CNRS) (FR)

( * ) Notice: Subject to any disclaimer, the term of this patent is extended or adjusted under 35 U.S.C. 154(b) by 0 days. days.

(21) Appl. No.: 15/101,255

(22) PCT Filed: Dec. 1, 2014

(86) PCT No.: PCT/EP2014/076081
§ 371 (c)(1),
(2) Date: Jun. 2, 2016

(87) PCT Pub. No.: WO2015/082392
PCT Pub. Date: Jun. 11, 2015

(65) Prior Publication Data
US 2016/0304826 A1    Oct. 20, 2016

(30) Foreign Application Priority Data
Dec. 6, 2013    (FR) ..................... 13 62258

(51) Int. Cl.
*G01N 35/08* (2006.01)
*C12M 1/26* (2006.01)
(Continued)

(52) U.S. Cl.
CPC ............ *C12M 33/04* (2013.01); *C12M 23/16* (2013.01); *C12M 29/04* (2013.01); *C12M 29/10* (2013.01);
(Continued)

(58) Field of Classification Search
CPC ....... G01N 35/08; C12M 29/04; C12M 29/10; C12M 33/04
(Continued)

(56) References Cited

U.S. PATENT DOCUMENTS 4,102,179 A * 7/1978 Snell ....................... G01N 30/38
                                                           210/656
4,835,707 A * 5/1989 Amano .................... C12Q 1/00
                                                           422/62

(Continued)

FOREIGN PATENT DOCUMENTS

| FR | 2957086 A1 | 9/2011 |
| FR | 2957087 A1 | 9/2011 |
| WO | 2005019805 A1 | 3/2005 |

OTHER PUBLICATIONS

Dinwoodie, R. C. et al, Biotechnology and Bioengineering 1985, 27, 1060-1062.*

(Continued)

*Primary Examiner* — Arlen Soderquist
(74) *Attorney, Agent, or Firm* — Lerner, David, Littenberg, Krumholz & Mentlik, LLP

(57) ABSTRACT

The invention concerns a facility for coupling a bioreactor for culturing bio-organisms, in dynamic mode, with at least one device for physicochemically analyzing a fluid from this (Continued)

Figure 1:
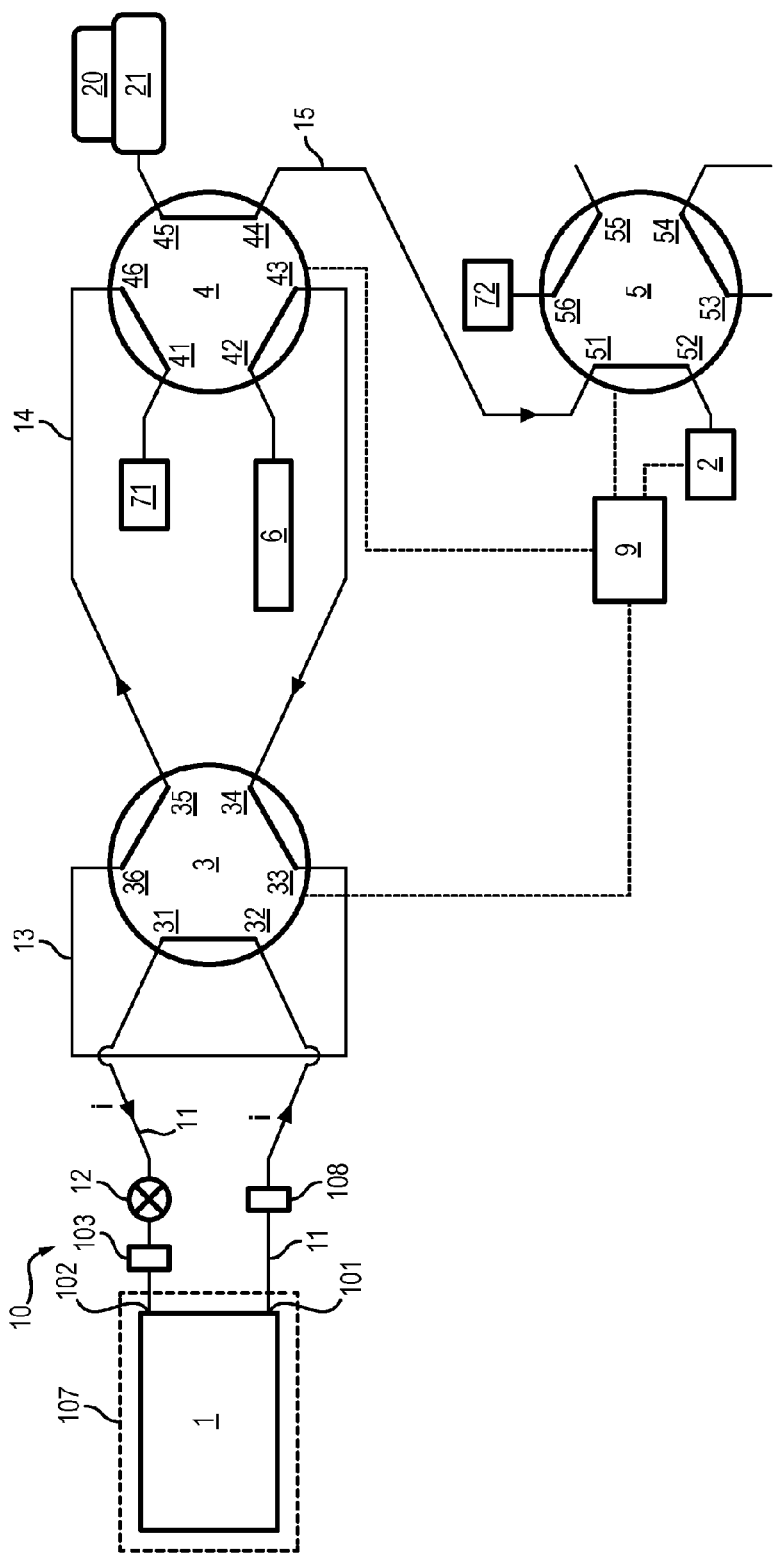

bioreactor or collecting samples of this fluid, the device being equipped with a pump and an injector, the bioreactor being equipped with means for supplying culture medium and xenobiotic(s). The facility is remarkable in that the bioreactor is connected to a closed perfusion loop provided with a pump, fitted with a sampling loop and in that the facility comprises:

- a device for injecting a cleaning product into said sampling loop,
- two six-way valves, the first valve being connected to the closed perfusion loop, to the sampling loop and to a cleaning loop, the second valve being connected to the cleaning loop and an injection loop that connects the injector to at least one of the devices.

14 Claims, 3 Drawing Sheets

(51) Int. Cl.
  *C12M 1/00* (2006.01)
  *C12M 1/34* (2006.01)
  *C12M 3/06* (2006.01)
  *C12Q 1/02* (2006.01)

(52) U.S. Cl.
  CPC ............ *C12M 41/12* (2013.01); *C12M 41/32* (2013.01); *C12M 41/34* (2013.01); *C12M 43/00* (2013.01); *C12Q 1/02* (2013.01)

(58) Field of Classification Search
  USPC .................. 422/70, 81; 436/52, 173, 180
  See application file for complete search history.

(56) References Cited

U.S. PATENT DOCUMENTS

| | | | | |
|---|---|---|---|---|
| 5,462,660 | A * | 10/1995 | Singleton | B01D 15/14 210/198.2 |
| 6,063,284 | A * | 5/2000 | Grill | B01D 15/1814 210/198.2 |
| 6,080,318 | A * | 6/2000 | Gumm | B01D 15/1885 210/198.2 |
| 6,324,924 | B1 * | 12/2001 | Peterson | G01N 35/1097 73/863 |
| 6,668,624 | B2 * | 12/2003 | Tani | G01N 30/06 422/68.1 |
| 7,588,725 | B2 * | 9/2009 | Ozbal | B01F 5/0085 210/141 |
| 8,507,266 | B2 * | 8/2013 | Welter | C12M 23/24 435/289.1 |
| 2002/0134142 | A1 * | 9/2002 | Tani | G01N 30/06 73/61.56 |
| 2005/0019216 | A1 * | 1/2005 | Trutnau | G01N 21/553 422/81 |
| 2005/0029196 | A1 * | 2/2005 | Rhemrev-Boom | B01D 15/3804 210/656 |
| 2005/0194318 | A1 * | 9/2005 | Ozbal | B01F 5/0085 210/656 |
| 2006/0281143 | A1 * | 12/2006 | Liu | C12M 23/34 435/34 |
| 2007/0020751 | A1 | 1/2007 | Bradamante et al. | |
| 2007/0062876 | A1 * | 3/2007 | Srinivasan | G01N 30/96 210/660 |
| 2011/0247405 | A1 * | 10/2011 | Yasunaga | G01N 30/18 73/61.55 |

OTHER PUBLICATIONS

Koliander, A. et al, Acta Biotechnologica 1990, 10, 387-394.*
Ozturk, S. S. et al, Biotechnology and Bioengineering 1995, 48, 201-206.*
Leggas, M. et al, Journal of Pharmaceutical Sciences 2004 93, 2284-2295.*
Forss, E. "On-line HPLC" Masters Thesis 2012, 34 pages.*
Van Midwoud et al: "On-line HPLC Analysis System for Metabolism and Inhibition Studies in Precision-Cut Liver Slices", Analytical Chemistry, vol. 83, No. I, Jan. 1, 2011 (Jan. 1, 2011), pp. 84-91.
Grist et al: "Microfluidic cell culture systems with integrated sensors for drug screening", Microfluidics, Biomems, and Medical Microsystems X, SPIE, 1000 20th St., Bellingham WA 98225-6705 USA, vol. 8251, No. 1, Mar. 8, 2012 (Mar. 8, 2012), pp. 1-12.
Van Midwoud et al: "Microfluidic devices for in vitro studies on liver drug metabolism and toxicity", Integrative Biology, vol. 3, No. 5, Jan. 1, 2011 (Jan. 1, 2011), p. 509.
Wu et al: "Microfluidic cell culture systems for drug research", Lab on a Chip, vol. 10, No. 8, Jan. 1, 2010 (Jan. 1, 2010), p. 939.
Prot et al: "The Current Status of Alternatives to Animal Testing and Predictive Toxicology Methods Using Liver Microfluidic Biochips", Annals of Biomedical Engineering, Kluwer Academic Publishers—Plenum Publishers, NE, vol. 40, No. 6, Dec. 10, 2011 (Dec. 10, 2011), pp. 1228-1243.
French Preliminary Search Report for Application No. FR 1362258 dated Oct. 15, 2014.

* cited by examiner

FACILITY FOR COUPLING A BIOREACTOR WITH A DEVICE FOR PHYSICOCHEMICALLY ANALYSING OR COLLECTING SAMPLES

CROSS REFERENCE TO RELATED APPLICATIONS

The present application is a national phase entry under 35 U.S.C. § 371 of International Application No. PCT/EP2014/076081, filed Dec. 1, 2014, published in French, which claims priority from French Patent Application No. 1362258, filed Dec. 6, 2013, the disclosures of which are incorporated by reference herein.

GENERAL TECHNICAL FIELD

The invention relates to the field of continuous and real-time, or almost continuous and real-time, analysis of a biological fluid coming from at least one bioreactor for culturing bio-organisms, such as cells, yeasts or bacteria, for example.

It relates more precisely to a coupling facility between this culturing bioreactor in dynamic mode and at least one physicochemical analysis unit, such as a liquid chromatography device or a mass spectrometer, for example or a unit for collecting samples.

PRIOR ART

Of bio-organism cultures, in vitro cellular cultures are increasingly being used in all phases of pharmaceutical research as they represent an advantageous alternative to in vivo models, i.e, to animal experimentation, to which both economic and ethical pressure is being applied at the international level.

These in vitro cultures cultivate cells from animal or human tissue or organ so that they mimic the biological behaviour of the tissue or organ taken in its natural environment, within a living organism.

These cellular cultures allow foreseeing the reaction of the tissue or natural organ vis-à-vis xenobiotics, i.e, molecules foreign to a living organism, for example drugs, pesticides, industrial pollutants.

More precisely, these cultures detect and analyse metabolites produced by the cells, (i.e, transformation and/or degradation products of the initial product), detect variations in the "metabolome" (i.e, the combination of metabolites and other molecules found in a biological fluid) and track and search for biomarkers. These cultures constitute an evaluation tool of the metabolism and toxicity of xenobiotics.

Currently, cellular cultures mainly form on Petri dishes. These dishes containing a nutritive medium and placed in an environment favourable to cellular growth are inseminated with the cells of the tissue or organ to be simulated. Once developed, they are put in contact with the xenobiotic to be analysed. Impact on the cells is then determined via sampling and analysis of the metabolites.

These Petri dishes have disadvantages.

First, they do not allow obtaining multilayer (three-dimensional) cell cultures, or keeping some categories of cells alive for a long time, especially primary hepatocytes, for example. It is fairly important to be able to study liver or kidney cells as these organs play a major role in metabolism of xenobiotics.

Also, this type of culture is incapable of reproducing the real behaviour of a tissue or organ in a living organism.

Also, cells on Petri dishes are cultivated in "static" conditions (i.e, without circulation of fluids) and not "dynamic", (with circulation of fluids), while the latter are rightly the only one likely to reflect the real behaviour of irrigated tissue or organ.

Finally, cultures on Petri dishes do not or barely study chronic exposure to xenobiotics in low doses.

For these reasons it has been proposed to replace the Petri dishes by bioreactors operating in "dynamic mode".

The notion of "dynamic mode" means that the fluid in which the culture bathes is circulated by a pump.

These bioreactors include "micro-fluidic biochips".

The "micro-fluidic biochip" designates a miniaturised device comprising a "micro-structured" culture chamber (or compartment), i.e, whereof at least one of the upper or lower walls has microstructures, i.e, ducts from a few tens to a few hundreds of micrometers, frequently between 20 µm and 500 µm.

These biochips enable cellular culture in three dimensions, in a dynamic and micro-fluidic environment and are therefore best able to reproduce in vitro the conditions observed in vivo.

Xenobiotics are introduced to the circulation loop of the nutritive fluid, upstream of the biochip and metabolites and biological markers are sampled downstream of the biochip.

These samplings are then analysed in measuring units such as liquid or gas chromatography units or a mass spectrometer.

If it is thus possible to take samplings at successive time intervals and analyse them, this technique does not continuously track metabolism of the studied xenobiotic.

Furthermore, if some of the biomarkers and metabolites produced are unstable, have brief shelf lives, or are products in low quantity, there is always a risk that they are not detected between two successive samplings.

But it could be interesting for example to track in real-time phenomena of cellular regeneration, cellular migrations or clearance (capacity of an organ to eliminate a given substance), track inflammation processes, transitory responses or even phenomena of cellular differentiation. With the above techniques this is not possible or at least is very difficult and the results obtained lack time precisions.

The article by Paul van Midwoud et al., "*On-line HPLC analysis system for metabolism and inhibition studies in precision-cut liver slices*", Anal. Chem. 2011, 83, 84-91, already discloses a coupling facility of a biochip having three chambers with a high-performance liquid chromatography analysis unit (HPLC). The biochip is fed upstream with culture medium and/or inhibitor to be studied. Furthermore, each of the three outputs of the biochip is connected to an injection loop, via a six-way valve, in turn mounted on the circuit of the HPLC unit between the pump and the analysis column.

Such a coupling facility allows injecting sequentially samples from one of the chambers of the biochip into the chromatography unit, once all the 30 minutes as mentioned in this article.

But, in this facility the supply circuit (perfusion) of the biochip is not closed. It eventuates that at regular intervals some of the fluids coming from the biochip are directed to a drain tank and do not return to enrich the biochip. Also, the injection loop can be fouled over the long term and cannot be cleaned.

PRESENTATION OF THE INVENTION

The aim of the invention is to resolve the above disadvantages of the prior art by proposing a facility which couples a culture bioreactor in dynamic mode to one or more physicochemical analysis or sample collecting units to perform real-time and continuous analysis of fluid coming from this bioreactor.

Another aim of the invention is to provide a facility which optionally traps a sample of fluid over a certain time period, prior to its injection into the analysis unit to boost concentration of the collected metabolites or biomarkers.

An additional aim of the invention is to provide a facility which can be cleaned easily and frequently, without as such contaminating the collected samples coming from the bioreactor.

Another aim of the invention is to provide a facility which avoids signal loss over time, in case of fouling or start of fouling of the analysis unit.

Finally, the proposed coupling facility should advantageously be easily transportable, simple to make and use.

For this purpose, the invention relates to a coupling facility of a bioreactor for culturing bio-organisms, in dynamic mode, with at least one unit for physicochemical analysis of fluid coming from this bioreactor or for collecting samples of this fluid, said unit being equipped with a pump and an injector, the bioreactor being equipped with means for supplying culture medium and xenobiotics.

According to the invention, the bioreactor is connected to a closed perfusion loop provided with a pump, this perfusion loop being fitted with a derivation loop, so-called "sample loop" and in that the facility comprises:
  an injection device of a cleaning product into said sample loop,
  a first valve comprising six ways,
  and a second valve comprising six ways,
  the first valve being connected to the closed perfusion loop, to the sample loop and to a cleaning loop, the second valve being connected to the cleaning loop and to an injection loop which connects the injector to at least one of the units for physicochemical analysis or collecting samples.

According to other advantageous and non-limiting characteristics of the invention, taken singly or in combination:
  the facility comprises a third valve fitted with at least one input and two outputs, this third valve being positioned on the injection loop, such that its input is connected to the injector, its first output is connected to at least one of the units for analysis or collecting and its second output is connected to a drain tank, said third valve occupying either a first position in which the input is connected to its first output, or a second position in which the input is connected to its second output;
  for the first valve, its first and second connecting orifices are connected to the closed perfusion loop of the bioreactor, its third and sixth connecting orifices are connected to the sample loop, its fourth connecting orifice to the third connecting orifice of the second valve and its fifth connecting orifice to the sixth connecting orifice of the second valve, said first valve occupying either a first position, in which its first connecting orifice is connected to its second, its third to its fourth and its fifth to its sixth, or a second position, in which its first connecting orifice is connected to its sixth, its second to its third and its fourth to its fifth,
  for the second valve, its first connecting orifice is connected to a drain tank, its second connecting orifice to the injection device of a cleaning product, its fifth connecting orifice to the injector and its fourth connecting orifice to at least one of the physicochemical analysis units, this second valve occupying either a first position in which its first connecting orifice is connected to its second, its third to its fourth and its fifth to its sixth, or a second position in which its first connecting orifice is connected to its sixth, its second to its third and its fourth to its fifth;
  the fourth connecting orifice of the second valve is connected to the input of the third valve;
  the sample loop includes a trapping column;
  a filter is present on the perfusion loop between the bioreactor and the first valve;
  the bioreactor is placed inside an enclosure in which the rate of carbon dioxide and the temperature are controlled;
  the physicochemical analysis unit is a liquid chromatography unit;
  the physicochemical analysis unit is a high-performance liquid chromatography unit HPLC;
  the physicochemical analysis unit is selected from a mass spectrometer, especially a mass spectrometer provided with a source of ionisation for liquid of type ESI, APCI or APPI, a nuclear magnetic resonance unit NMR, a fluorometric detector, a spectrophotometer or an online coupling unit MALDI TOF;
  the unit is a collector of fractions for collecting samples of fluid coming from the bioreactor;
  the facility comprises one or more physicochemical analysis units, mounted in series after a first physicochemical analysis unit, this first unit being especially a liquid chromatography unit;
  the bioreactor is a multi-reactor box;
  the bioreactor is a biochip;
  the biochip is of type micro-fluidic.

The invention also relates to a process for online physicochemical analysis of a biological fluid coming from a bioreactor or for collecting samples of this fluid with the above facility, which consists of performing at least once the following cycle of steps:
  a) putting the first valve in its first position and the second valve in its second position, so as to clean and dry the sample loop,
  b) putting the first valve and the second valve in their second position, so as to collect a sample in the sample loop and inject an internal standard into the unit, from the injector,
  c) putting the first valve and the second valve in their first position, so as to inject the sample collected into the sample loop, in the unit, by means of an eluent provided by the injector.

PRESENTATION OF FIGURES

Figure 2:
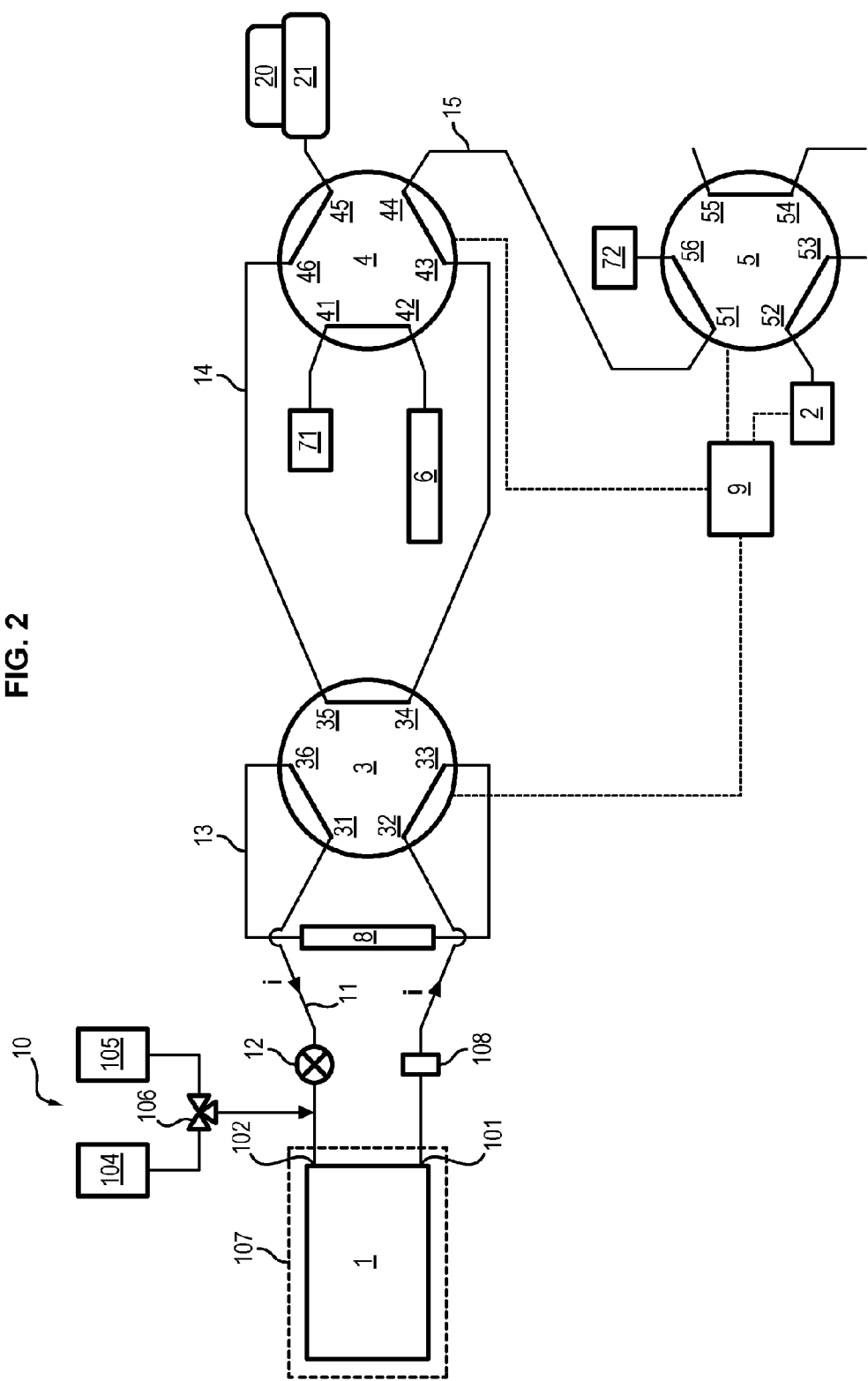
Figure 3:
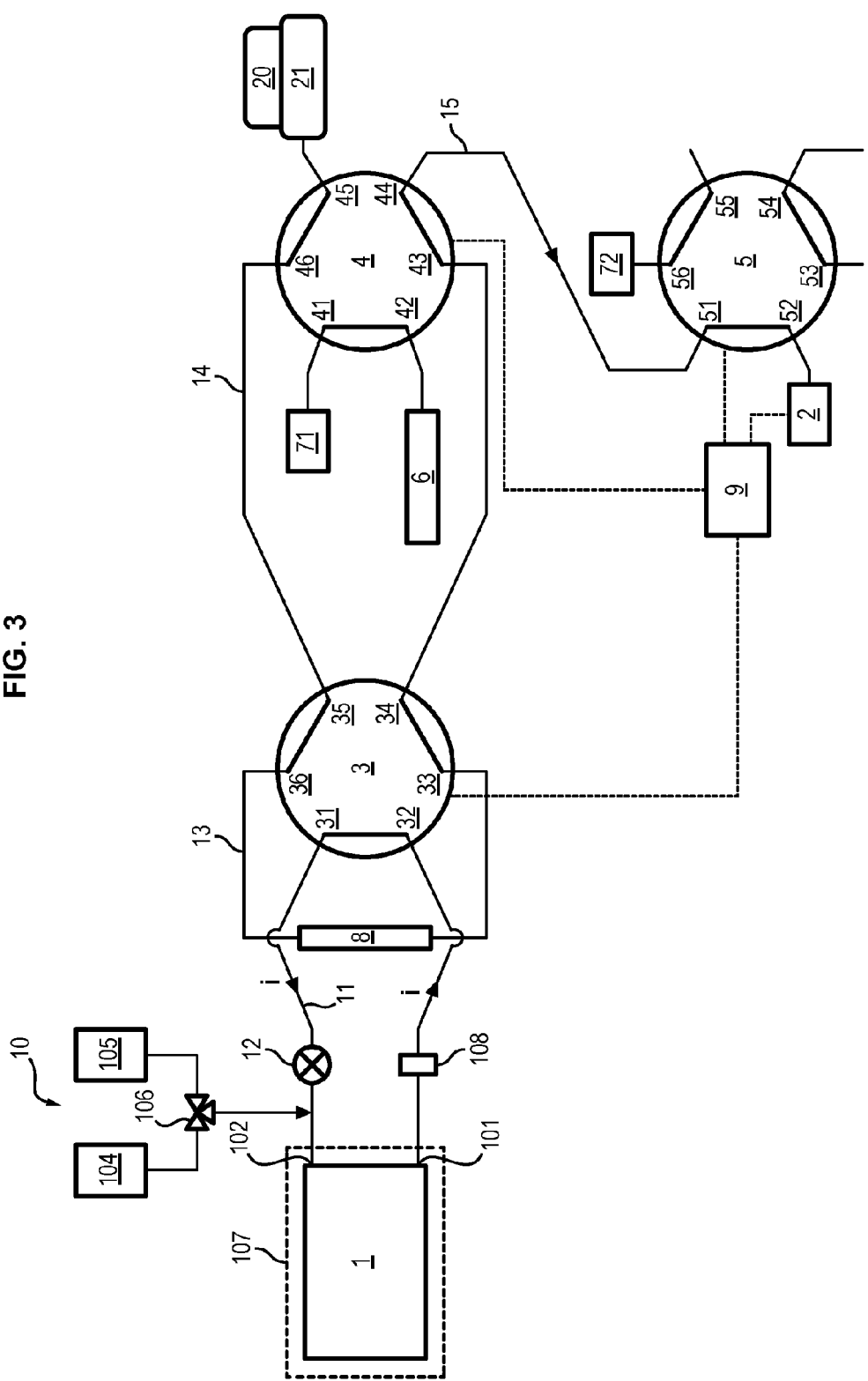

Other characteristics and advantages of the invention will emerge from the following description in reference to the appended drawings which illustrate different possible embodiments by way of indication but non-limiting, in which:

FIGS. 1 to 3 are drawings showing different embodiments of the coupling facility according to the invention, in three different operating states.

DETAILED DESCRIPTION

In reference to the above figures it is clear that the facility according to the invention couples a bioreactor 1 with at least one unit 2.

The bioreactor 1 is of the type which enables culture of bio-organisms, in dynamic mode.

The bio-organisms are preferably cells but can also be bacteria or yeasts for example.

The bioreactor comprises one or more compartments inside which the bio-organisms are cultivated.

The bioreactor 1 is fitted with a closed perfusion loop 11 which connects its output 101 to its input 102. Also, a pump 12 is installed, for example on the return line of this closed perfusion loop 11 so as to keep the biological fluid in circulation. The direction of circulation is shown by arrows i.

The pump 12 is preferably a peristaltic pump which draws fluid present in the flexible tube constituting the loop 11 by compression and deformation of the latter from the exterior. Such a pump is particularly adapted to small flows and does not risk contaminating fluid as it comprises no elements in direct contact with the latter.

The bioreactor 1 is further equipped with means 10 for supplying culture medium.

According to a first embodiment shown in FIG. 1, these means 10 consist of a tank 103 connected to the perfusion loop 11, downstream of the pump 12 and upstream of the input 102 of the bioreactor 1. The culture medium is placed in this tank and is renewed as needed. Also, the xenobiotic(s) are introduced to this tank 103 for analysis reasons. The pump 12 allows feeding the bioreactor 1 with culture medium, but also recirculating the fluid which exits from there.

According to a second embodiment shown in FIGS. 2 and 3, the means 10 consist of an automated device which comprises a tank 104 for culture medium, a tank 105 for xenobiotics, both connected to a three-way valve 106 whereof the output is in turn connected at a point of the closed loop 11, located between the pump 12 and the input 102 of the bioreactor 1.

The bioreactor 1 can for example be a multi-reactor box which comprises several compartments of cultures, preferably micro-structured, each being connected to an input port via an input well and to an output port via an output well. "Micro-structured" compartment means that the volume of liquid which is stored in it is a few microliters. Examples of such multi-reactor boxes are described for example in documents FR 2 957 086 and FR 2 957 087.

The bioreactor 1 can also consist of a biochip microfluidic or not, which comprises in this case a single culture compartment.

Preferably, the bioreactor 1 is arranged inside an enclosure 107 inside which the rate of carbon dioxide ($CO_2$) and the temperature are controlled so as to maintain optimal culture conditions of bio-organisms present in this bioreactor.

Finally, it is seen advantageously that a filter 108 can be arranged on the perfusion loop 11, between the bioreactor 11 and the connecting orifice 32 of the valve 3.

By way of advantage, the bioreactor and its enclosure 107 have sufficiently small dimensions to be portable and especially transportable near the units 2, 2'.

The unit 2 is connected to an injector 21, via an injection loop 15.

This injector 21 is itself connected to a pump 20, mounted on a tank not shown in the figures.

The injector 21 sends to the unit 2 by choice either an eluent or a standard for calibrating and benchmarking the curves obtained by the unit 2, as will be specified later.

According to a first variant embodiment the facility comprises a single unit 2.

Preferably, this unit 2 is a liquid phase chromatography unit, (for example of HPLC type), which conducts quantitative, qualitative and separative analysis of the fluid coming from the bioreactor 1. This type of chromatography is based on separation of compounds drawn along by the eluent, via a stationary phase.

However, this unit 2 can also be a physicochemical analysis unit, for example selected from:

a mass spectrometer, especially a mass spectrometer provided with a source of ionisation for liquid of type electro spray ionisation (ESI), of type atmospheric pressure chemical ionisation (APCI) or of type atmospheric pressure photo ionisation (APPI), an analysis nuclear magnetic resonance unit (NMR), a fluorometric detector, a spectrophotometer or an online coupling unit of type "MALDI TOF".

A unit of type "MALDI-TOF" is a mass spectrometer coupling a source of laser ionisation assisted by a "MALDI" matrix, (Matrix-Assisted Laser Desorption/Ionisation) and a time-of-flight analyser ("TOF", "time-of-flight mass spectrometry").

According to a second variant embodiment, one or more units 2 can be mounted in series behind a first unit 2, this first unit preferably being but not compulsorily a liquid chromatography unit and the other units being selected from the above list.

The molecules separated by this liquid chromatography unit are analysed by the analysis unit(s) mounted in series behind.

Finally, according to another variant embodiment, the above analysis unit(s) 2 can be replaced by a single collector of fractions, which collects samples of fluid coming from the bioreactor 1, accompanied optionally by an internal standard, to be able to analyse them with another unit, arranged for example in a remote laboratory.

Advantageously, the injection loop 15 is equipped with a three-way valve 5. This comprises a connecting input 51 connected to the loop 15 and two outputs, one 52 connected to the unit 2 and the other 56 connected to a drain tank 72.

In the first position of the valve 5, shown in FIG. 1, the input 51 is connected to the output 52, such that the contents of the injection loop 15 is sent to the unit 2. In the second position, shown in FIG. 2, this content is sent to the drain 72.

This three-way valve 5 could be replaced by a valve equipped with a greater number of ways, for example six, as shown in the figures. In this case the connecting orifices 53, 54 and 55 are blocked by plugs.

The coupling facility between the bioreactor 1 and the unit(s) 2 will now be described in more detail.

In general, this facility comprises a sample loop 13, a cleaning loop 14 and two six-way valves, respectively a first valve 3 and a second valve 4.

A six-way valve comprises a body fitted with six connecting orifices, as well as a blocking element (valve), moveable between two positions. This moveable element connects the connecting orifices in pairs. As a function of the position of the moveable element, different connecting orifices are connected to each other.

The sample loop 13 is a loop which forms a derivation from the closed perfusion loop 11.

As is clear from the figures, the first and second connecting orifices 31, 32 of the valve 3 are connected to the two ends of the perfusion loop 11. Also, the third and sixth connecting orifices 33, 36 of this same valve are connected to the two ends of the sample loop 13.

In the first position of the valve 3 shown in FIG. 1, the loops 11 and 13 are not connected and the perfusion of the bioreactor 1 is kept.

In the second position of the valve 3 shown in FIG. 2, the first and sixth connecting orifices 31, 36 are connected together as are the second and third orifices 32, 33 such that the sample loop 13 is in fluid connection with the loop 11 and consists of an extension of the latter. In this way, perfusion of the bioreactor 1 is continued during the collecting phase of the sample.

The sampling loop 13 is a loop with constant fluid volume. This volume, which corresponds to that of the collected sample, is determined by the length and diameter of the tube used to form this loop 13.

According to the variant embodiment of the FIG. 2, this derivation loop 13 can also comprise a trapping column 8 which retains and therefore concentrates some molecules or metabolites, while the rest of the fluid returns to irrigate the bioreactor 1.

The cleaning loop 14 connects an injection device 6 of a cleaning product to a drain tank 71, via the valves 3 and 4. This cleaning product is preferably compressed air or air containing added product such as acetone for example.

More precisely, the device 6 is connected to the second connecting orifice 42 of the valve 4, the third orifice 43 is connected to the fourth orifice 34 of the valve 3, the fifth orifice 35 of the valve 3 is connected to the sixth orifice 46 of the valve 4 and finally the first orifice 41 is connected to the drain tank 71, capable of collecting any residue of products pushed by air and/or acetone.

In the first position of the valve 4, shown in FIG. 2, the connecting orifices are connected in pairs, as follows: 41 and 42, 43 and 44, 45 and 46. The device 6 is connected directly to the drain 71 and the sample loop 13 is not cleaned.

To the contrary, in the second position of the valve 4, shown in FIG. 1, the orifices 41 and 46 on the one hand and 42 and 43 on the other hand are connected and the loop 13 is cleaned and/or dried, so long as the valve 3 is in the first position.

All the valves 3, 4 and 5 are electrovalves, controlled remotely by a control unit 9 which can optionally be integrated into one of the physicochemical analysis units 2.

The different steps of the process for physicochemical analysis or collecting samples likely to be placed by means of this facility will now be described in more detail.

Step 1:

The first valve 3 is placed in its first position (FIG. 1), the second valve 4 in its second position (FIG. 1) and the valve 5 in its second position (FIG. 2).

The culture is kept in dynamic mode in the bioreactor 1 since the biological fluid circulates in the loop 11 via the pump 12 and returns to the bioreactor. The sample loop 13 and the trapping column 8, if present, are cleaned and/or dried. Finally, the eluent is sent by the injector 21 in the direction of the drain tank 72.

Step 2:

The valve 3 is toggled in its second position (FIG. 2), the valve 4 in its second position (FIG. 2) and the valve 5 in its first position (FIG. 1).

An internal standard is injected from the injector 21 via the loop 14, the connecting orifices 35 and 34 of the valve 3, then the orifices 43 and 44 of the valve 4, into the unit. This internal standard eliminates fouling of this unit. In fact, biological fluids (culture media, serum etc . . . ) tend to foul these units. No cleaning of the units can be done during the analysis cycle. This internal standard sets a reference which serves to target and calibrate the curves obtained by means of the units and limit signal loss over time, (especially for analysis periods above 24 hours).

It is the injection of this internal standard which triggers toggling of the valve 3 in the above position. Because of this, the sample loop 13 is connected to the loop 11, which collects a sample in the injection loop 13, or even traps this sample in the trapping column 8. In this latter case, circulation via the loops 11 and 13 is maintained until enough concentration of metabolites is obtained in the column 8.

Step 3:

Next, and as shown in FIG. 3, the valves 3, 4 and 5 are placed in their first position.

In this case, the eluent injected by the injector 21 passes through the loop 14, then the sample loop 13 and accordingly draws the volume of sample lying in this loop 13, right into the unit(s).

The above cycle can then be repeated, which recleans the sample loop 13, prior to fresh analysis or fresh sampling (collecting).

The facility according to the invention has many advantages.

It conducts continuous or almost continuous analyses (with the exception of the cleaning period) of fluids produced by the bioreactor and maintains the latter in dynamic culture mode.

It cleans the sample loop 13 without polluting the perfusion loop 11. By way of advantage a bubble trap can be present in the perfusion loop 11 for trapping air still present in the loop 13 and which could be drawn there during toggling of the valve 3 in the second position.

By way of injection of the internal standard, it conserves a high level of precision of the signal obtained by the analysis units 2, even for long analysis periods (of at least 24 hours).

Finally, the facility can be easily disassembled and transported to near analysis units and different bioreactors can easily be connected to the facility to conduct successive analyses.

The invention claimed is:

1. A coupling facility of a bioreactor for culturing bioorganisms, in dynamic mode, with at least one unit for physicochemical analysis of fluid coming from this bioreactor or one unit for collecting samples of this fluid, said unit being equipped with a pump and an injector, the bioreactor being equipped with means of supplying culture medium and xenobiotic(s), wherein the bioreactor is connected to a closed perfusion loop provided with a pump, this perfusion loop being fitted with a derivation loop, so-called "sample loop" and in that the facility comprises:

an injection device of a cleaning product into said sample loop, a first valve comprising six ways, and a second valve comprising six ways, wherein the first and second valves each have first, second, third, fourth, fifth and sixth connecting orifices, the first and second valves are movable between a first position in which the first connecting orifice is connected to the second connecting orifice, the third connecting orifice to the fourth connecting orifice and the fifth connecting orifice to the sixth connecting orifice, and a second position, in which the first connecting orifice is connected to the sixth connecting orifice, the second connecting orifice to the third connecting orifice and the fourth connecting orifice to the fifth connecting orifice, wherein for the first valve, its first and second connecting orifices are connected to the closed perfusion loop of the bioreactor, its third and sixth connecting orifices are connected to the sample loop, its fourth connecting orifice to the third connecting orifice of the second valve through a cleaning loop and its fifth connecting orifice to the sixth connecting orifice of the second valve through the cleaning loop, and wherein for the second valve, its first connecting orifice is connected to a drain tank, its second connecting orifice to the injection device of a cleaning product, its fifth connecting orifice to the injector and its fourth connecting orifice to at least one of the units for physicochemical analysis or collecting samples, through an injection loop.

2. The facility according to claim 1, wherein it comprises a third valve fitted with at least one input and two outputs, this third valve being positioned on the injection loop such that its input is connected to the injector through the fourth connecting orifice and the fifth connecting orifice of the second valve, its first output is connected to at least one of the units for physicochemical analysis or collecting samples and its second output is connected to a drain tank, said third valve occupying either a first position in which the input is connected to its first output, or a second position in which the input is connected to its second output.

3. The facility according to claim 1, wherein the sample loop includes a trapping column.

4. The facility according to claim 1, wherein a filter is present on the perfusion loop between the bioreactor and the first valve.

5. The facility according to claim 1, wherein the bioreactor is placed inside an enclosure in which the rate of carbon dioxide and the temperature are controlled.

6. The facility according to claim 1, wherein the physicochemical analysis unit is a liquid chromatography unit.

7. The facility according to claim 6, wherein the physicochemical analysis unit is a high-performance liquid chromatography unit (HPLC).

8. The facility according to claim 1, wherein the physicochemical analysis unit is selected from a mass spectrometer, especially a mass spectrometer provided with a source of ionisation for liquid of type ESI, APCI or APPI, a nuclear magnetic resonance unit (NMR), a fluorometric detector, a spectrophotometer or an online coupling unit MALDI TOF.

9. The facility according to claim 1, wherein the unit is a collector of fractions for collecting samples of fluid coming from the bioreactor.

10. The facility according to claim 1, wherein it comprises one or more physicochemical analysis units, mounted in series after a first physicochemical analysis unit, this first unit being especially a liquid chromatography unit.

11. The facility according to claim1, wherein the bioreactor is a multi-reactor box.

12. The facility according to claim 1, wherein the bioreactor is a biochip.

13. The facility according to claim 12, wherein the biochip is of micro-fluidic type.

14. A process for online physicochemical analysis of a biological fluid coming from a bioreactor or for collecting samples of this fluid, with the facility according to claim 1, wherein it consists of performing at least once the following cycle of steps:

a) putting the first valve in its first position and the second valve in its second position, so as to clean and dry the sample loop, b) putting the first valve and the second valve in their second position, so as to collect a sample in the sample loop and inject an internal standard in at least one of a first unit for physicochemical analysis of fluid coming from the bioreactor or a second unit for collecting samples of this fluid from the injector, c) putting the first valve and the second valve in their first position, so as to inject the sample collected into the sample loop, in said first or second unit, by means of an eluent provided by the injector.

* * * * *